United States Patent
Markosyan

(10) Patent No.: US 12,402,645 B2
(45) Date of Patent: Sep. 2, 2025

(54) HIGH-PURITY MOGROSIDES AND PROCESS FOR THEIR PURIFICATION

(71) Applicant: PURECIRCLE SDN BHD, Bandar Enstek (MY)

(72) Inventor: Avetik Markosyan, Kuala Lumpur (MY)

(73) Assignee: PureCircle Sdn. Bhd., Negeri Sembilan (MY)

(*) Notice: Subject to any disclaimer, the term of this patent is extended or adjusted under 35 U.S.C. 154(b) by 661 days.

(21) Appl. No.: 17/865,745

(22) Filed: Jul. 15, 2022

(65) Prior Publication Data

US 2022/0346411 A1  Nov. 3, 2022

Related U.S. Application Data

(60) Continuation of application No. 14/792,594, filed on Jul. 6, 2015, now Pat. No. 11,419,351, which is a division of application No. 13/219,721, filed on Aug. 29, 2011, now Pat. No. 9,101,162.

(60) Provisional application No. 61/379,729, filed on Sep. 3, 2010.

(51) Int. Cl.
| | |
|---|---|
| A23L 2/60 | (2006.01) |
| A23L 27/30 | (2016.01) |
| A24B 13/00 | (2006.01) |
| A61K 8/63 | (2006.01) |
| A61K 8/97 | (2017.01) |
| A61K 8/9789 | (2017.01) |
| A61K 8/9794 | (2017.01) |
| A61Q 19/00 | (2006.01) |
| C07J 17/00 | (2006.01) |
| G01N 30/02 | (2006.01) |

(52) U.S. Cl.
CPC ............ *A23L 2/60* (2013.01); *A23L 27/36* (2016.08); *A61K 8/63* (2013.01); *A61K 8/97* (2013.01); *C07J 17/005* (2013.01); *A23L 27/34* (2016.08); *A23V 2002/00* (2013.01); *A23V 2250/24* (2013.01); *A23V 2250/254* (2013.01); *A23V 2300/14* (2013.01); *A24B 13/00* (2013.01); *A61K 8/9789* (2017.08); *A61K 8/9794* (2017.08); *A61Q 19/00* (2013.01); *G01N 2030/027* (2013.01)

(58) Field of Classification Search
CPC ............ A23L 2/60; A23L 33/105; A23L 5/51; A23V 2250/24; A23V 2250/254; A23V 2300/14

See application file for complete search history.

(56) References Cited

U.S. PATENT DOCUMENTS

| | | | |
|---|---|---|---|
| 6,124,442 A | 9/2000 | Zhou et al. | |
| 6,228,996 B1 | 5/2001 | Zhou et al. | |
| 9,101,162 B2 | 8/2015 | Markosyan | |
| 2007/0116819 A1 | 5/2007 | Prakash et al. | |
| 2008/0108710 A1 | 5/2008 | Prakash et al. | |
| 2009/0162529 A1* | 6/2009 | Shi | A23L 33/21 426/658 |
| 2009/0196966 A1 | 8/2009 | West et al. | |
| 2010/0267847 A1 | 10/2010 | Yoshinaka et al. | |

FOREIGN PATENT DOCUMENTS

| | | |
|---|---|---|
| CN | 101029071 | 9/2007 |
| CN | 101050230 | 10/2007 |
| CN | 101407535 | 4/2009 |
| JP | 2001211854 | 8/2001 |
| WO | 9418855 | 9/1994 |
| WO | 2007/062087 | 5/2007 |
| WO | 2008/030121 | 3/2008 |
| WO | 2008149253 | 12/2008 |

(Continued)

OTHER PUBLICATIONS

Yang et al., "Grosmomoside I, a new curcubitane triterpenoid glycoside from fruits of Momordica grosvenori," Chinese Traditional and Herbal Drugs 36(9), 1285-90 (2005). (Year: 2005).*
Extended European Search Report of patent application No. EP11179246.1 completed on Oct. 27, 2011 and mailed Nov. 11, 2011 (6 pages).
Communication pursuant to Article 94(3) EPC of European patent application No. EP11179246.1 mailed Oct. 17, 2012 (4 pages).
Kim et al., "Natural High Potency Sweetners", Handbook of Sweeteners, by Marie et al. (Eds), Springer Science + Business Media (New York), pp. 116-185, copyright 1991.
Xia et al., "Isolation of the Sweet Components from Siraitia Grosvenorli" Food Chem. 107, pp. 1022-1028 (2008).

(Continued)

*Primary Examiner* — Theodore R. Howell

(57) ABSTRACT

The present invention provides a process for preparation of highly purified mogrosides mixture from low purity mogrosides mixture. The process comprises providing a mixture of low purity mogrosides, dissolving the low purity mogrosides mixture in water or an aqueous alcohol solution to form an initial solution of mogrosides, passing the initial solution through a column system, wherein the column system comprises a plurality of columns, and each column is packed with a sorbent having different affinities to impurities and mogrosides so that one or more columns retains more mogrosides than other columns, washing the columns to remove impurities with an acidic aqueous solution, a basic aqueous solution, and an aqueous alcoholic solution successively, eluting the columns with an aqueous alcohol solution that contains higher alcohol content than the aqueous alcohol solution used in the washing step, wherein the eluate from the columns with high content of mogrosides are combined, and drying the combined eluate to obtain high purity mogrosides with the content of the total mogrosides are more than 70% (w/w). The present invention also provides a sweetener mixture and product comprising high purity mogrosides.

5 Claims, No Drawings

(56) References Cited

FOREIGN PATENT DOCUMENTS

WO     2009/023975     2/2009
WO     2009063921     5/2009

OTHER PUBLICATIONS

Extended European Search Report of patent application No. EP13160563.6 completed Jun. 19, 2013 and mailed Jun. 28, 2013 (5 pages).

* cited by examiner

HIGH-PURITY MOGROSIDES AND PROCESS FOR THEIR PURIFICATION

CROSS-REFERENCE TO RELATED APPLICATIONS

This application is a continuation of U.S. application Ser. No. 14/792,594 filed on Jul. 6, 2015, now allowed, which is a divisional of U.S. patent application Ser. No. 13/219,721, filed Aug. 29, 2011, now U.S. Pat. No. 9,101,162, which claims the benefit of US provisional application entitled "High-Purity Mogrosides" filed Sep. 3, 2010 having Ser. No. 61/379,729.

FIELD OF THE INVENTION

The invention relates to a process for purification of high purity mogrosides from *Siraitia grosvenori* fruit extract, particularly high purity mogrosides mixtures with high mogroside V content, and further to high purity mogrosides and their applications in food and beverage products.

DESCRIPTION OF THE RELATED ART

Luo han guo generally refers to a fruit of *Siraitia grosvenori*, a member of the Cucurbitaceae family, is a plant native to some regions of southern Asia and China. The sweet taste of luo han guo mainly comes from triterpene glycosides generally known as mogrosides or mogrol glycosides. Mogrosides comprise only about 1% of the luo han guo fruit. There are a number of mogrosides identified in luo han guo but generally mogroside V (CAS No: 88901-36-4) has the highest concentration compared to others (Table 1). Mogrol glycosides have the same core molecule—mogrol or oxo-mogrol and differ from each other by number and type of glycosidic residues bonded to mogrol or oxo-mogrol molecules.

TABLE 1

Mogrosides present in Luo han guo fruits

| Substance | Mol. Formula | Mol. Weight |
| --- | --- | --- |
| Mogroside IIE | $C_{42}H_{72}O_{14}$ | 801.01 |
| Mogroside III | $C_{48}H_{82}O_{19}$ | 963.15 |
| Mogroside IV | $C_{54}H_{92}O_{24}$ | 1125.29 |
| Mogroside V | $C_{60}H_{102}O_{29}$ | 1287.43 |
| Mogroside VI | $C_{66}H_{112}O_{34}$ | 1449.58 |
| 11-oxo-Mogroside V | $C_{60}H_{100}O_{29}$ | 1285.42 |
| Siamenoside I | $C_{54}H_{92}O_{24}$ | 1125.29 |
| Grosmomoside I | $C_{54}H_{92}O_{24}$ | 1125.29 |

Various extraction techniques are used to isolate mogrosides from luo han guo fruits. As a result luo han guo powdered extracts are being prepared which usually contain 30-65% w/w of total mogrosides, and mogroside V content of those materials can vary as much as 18-55%. Such extracts generally cannot be used as a sweetener in foods and beverages as they contain substantial amount of impurities; some of the impurities possess undesirable organoleptic properties, thus affecting the color, flavor, odor and taste profile of luo han guo extract.

Non-limiting examples of such impurities include proteins, pigments, polysaccharides, aldehydes, unsaturated aldehydes, methyl ketones, butyl crotonate, and phenolic compounds.

Hence there is a need for a commercially viable process for enhancing mogrosides content, particularly mogroside V content from low purity luo han guo preparations and removing the undesirable impurities so as to significantly improve the organoleptic characteristics of luo han guo preparations and thus allowing their usage in food.

No techniques are currently available for purifying of low purity luo han guo extract into high purity mogrosides. Therefore, there is a need for a process of for purification of high purity mogrosides from *Siraitia grosvenori* fruit extract.

SUMMARY OF THE INVENTION

The invention relates to a process for preparation of high purity mixtures of mogrosides from *Siraitia grosvenori* fruit extract.

In one embodiment, the process for preparation of highly purified mogrosides mixture from low purity mogrosides mixture comprises:

a. providing a mixture of low purity mogrosides;

b. dissolving the low purity mogrosides mixture in water or an aqueous alcohol solution to form an initial solution of mogrosides;

c. passing the initial solution through a column system, wherein the column system comprises a plurality of columns, and each column is packed with a sorbent having different affinities to impurities and mogrosides so that one or more columns retains more mogrosides than other columns;

d. washing the columns to remove impurities with an acidic aqueous solution, a basic aqueous solution, and an aqueous alcoholic solution successively;

e. eluting the columns with an aqueous alcohol solution that contains higher alcohol content than the aqueous alcohol solution used in the washing step, wherein the eluate from the columns with high content of mogrosides are combined; and f. drying the combined eluate to obtain high purity mogrosides with the content of the total mogrosides are more than 70% (w/w).

In another embodiment of the process, in the washing step (d), the water to alcohol ratio (vol/vol) in the aqueous alcoholic solution is 99.9:0.1 to 60:40, and wherein in the eluting step (e), the water to alcohol ratio (vol/vol) of the aqueous alcoholic solution is 60:40 to 0.1:99.9.

In another embodiment of the process, in the washing step (d), the acidic aqueous solution comprises HCl, and the basic aqueous solution comprises NaOH.

In another embodiment of the process, the aqueous alcoholic solution comprises alcohol that is selected from the group consisting of methanol, ethanol, n-propanol, 2-propanol, 1-butanol, and 2-butanol.

In another embodiment of the process, the sorbent is a macroporous polymeric adsorption resin capable of adsorbing mogrosides.

In another embodiment of the process, the plurality of columns are consecutively connected.

In another embodiment of the process, the plurality of columns are connected in parallel.

In another embodiment of the process, it further comprises:

g. dissolving the high purity mogrosides in water or an aqueous alcoholic solution to result in a solution of mogrosides;

h. passing the solutions of mogrosides through a sequence of ultrafiltration and/or nanofiltration membranes with MWCO size from 1000 to 2500 to increase the purity of mogrosides mixture (total mogrosides content, % dry basis); and i. drying the obtained mogrosides mixture solution to obtain highly purified mogrosides mixture.

The present invention further provides a sweetener mixture comprising the high purity mogrosides; wherein the high purity mogrosides are blended with another high intensity sweetener.

In one embodiment of the sweetener mixture, the another high intensity sweetener is selected from the group consisting of steviol glycosides including a purified sweet steviol glycoside mixture, stevioside, rebaudioside A, rebaudioside B, rebaudioside C, rebaudioside D, rebaudioside E, rebaudioside F, dulcoside A, dulcoside B, rubusoside, and stevia; siamenoside; mogroside IV; mogroside V; Luo Han Guo sweetener; monatin and its salts (monatin SS, RR, RS, SR); glycyrrhizic acid and its salts; curculin; thaumatin; monellin; mabinlin; brazzein; hernandulcin; phyllodulcin; glycyphyllin; phloridzin; trilobatin; baiyunoside; osladin; polypodoside A; pterocaryoside A; pterocaryoside B; mukurozioside; phlomisoside I; periandrin I; abrusoside A; cyclocarioside I; and combinations thereof.

The present invention also provides a product comprising the high purity mogrosides.

In one embodiment of the product, the product is selected from the group consisting of food, beverage, pharmaceutical composition, tobacco, nutraceutical, oral hygienic composition, or cosmetic.

One objective of the invention to develop an efficient method of preparation of highly purified mogro sides' mixture from low purity mogrosides' mixture.

Another objective of the invention is to develop a method of preparation of high mogroside V content luo han guo sweetener from low mogroside V content luo han guo sweetener.

DETAILED DESCRIPTION OF THE INVENTION

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention provides a process for purification of high purity mogrosides with high mogroside V content from *Siraitia grosvenori* fruit extract.

Hereinafter the term "mogrosides" refers to mogrol and oxo-mogrol glycosides, including mogroside IIE, mogroside IIB, mogroside III, mogroside IV, mogroside V, 11-oxo-mogroside V, mogroside VI, siamenoside I, and grosmomoside I.

Hereinafter the term "TM content" means the Total Mogrosides content, and it is calculated as the sum of 4 mogrosides including Mogroside V, 11-oxo-Mogroside V, Siamenoside I, and Grosmomoside I.

Hereinafter the term "highly purified" or "high purity" means the TM content of at least 70% (w/w) on dry basis.

Hereinafter the term "high mogroside V content" means the mogroside V content of at least 60% (w/w) on dry basis.

Hereinafter the term "low purity" means the TM content of less than 70% (w/w) on dry basis.

Hereinafter the term "low mogroside V content" means mogroside V content of less than 60% (w/w) on dry basis.

Hereinafter the reported purity levels are determined by HPLC method with following parameters. HPLC system—"Agilent 1200 series" (USA) equipped with degasser, quaternary pump, autosampler, thermostatted column compartment and DAD UV detector. Column—"YMC Polyamine II" 4.6×150 mm 5 µm (Japan) at 30° C.; mobile phase 70:30 (vol/vol) acetonitrile water at 1 mL/min; detector—UV at 204 nm. Reference standards of mogroside V, 11-oxo-mogroside V, siamenoside I, and grosmomoside I were obtained from "Chromadex Inc" (USA).

Hereinafter the term "impurity" means any compound other than mogrosides which are present in the mixture at more than 0.0001% (w/w) on dry basis. Non-limiting examples of impurities include proteins, pigments, polysaccharides, aldehydes, unsaturated aldehydes, methyl ketones, butyl crotonate, phenolic compounds as well as other non-mogroside compounds which may affect the organoleptic characteristics of luo han guo sweetener.

The process of purification of mogrosides of the present invention is applicable for any low purity mogrosides mixture with the TM content of less than 70% w/w on dry basis.

The present invention also provides a column system that can be used for the process of purification of mogrosides of the present invention. The column system is with following parameters. The column system comprises a plurality of columns that are connected in either consecutive (serial) or parallel manner, where the plurality of columns are of same or different volumes packed with a sorbent with different affinity to impurities and steviol glycosides. When the column system is used in parallel connection mode, the inlet of each column may connect to a separate feed source while the outlet to a separate receiver. The following description will highlight the mode of column connection specific for each particular stage. Within the same stage the system may function as an entity of several parallel and serial connected column groups and separate columns. The number of columns is 3-15. The ratio of volumes of first column to volume of second column is 1:1 to 1:10. The ratio of volumes of last column to volume of previous column is 3:1 to 1:10. The columns are packed with sorbent up to 75-100% of their total volume. The columns are maintained at temperature 5-80° C.

The alcohol is selected from the group consisting of alkanols, more particularly methanol, ethanol, n-propanol, 2-propanol, 1-butanol, 2-butanol.

The sorbent is any macroporous polymeric adsorption resin capable of adsorbing mogrosides, such as Amberlite® XAD series (Rohm and Haas), Diaion® HP series (Mitsubishi Chemical Corp), Sepabeads® SP series (Mitsubishi Chemical Corp), Cangzhou Yuanwei YWD series (Cangzhou Yuanwei Chemical Co. Ltd., China) or equivalent.

The process of the present invention comprises a few stages. In one embodiment, the first stage comprises passing an aqueous or aqueous alcoholic solution of low purity mogrosides mixture through a consecutively connected column system. The water to alcohol ratio (vol/vol) in the aqueous alcoholic solution is 99.9:0.1 to 60:40. As a result, the impurities and different mogrosides are retained in different sections of the column system. Impurities with high affinity are mostly retained in the first column, and low affinity impurities are mostly retained in the last column, while mogrosides are mostly retained in the middle columns of the column system. Lower molecular weight mogrosides, particularly siamenoside I and grosmomoside I, partially separated from higher molecular weight mogrosides, are retained at higher amounts in the first few columns of the middle columns of the column system, whereas higher molecular weight mogrosides, particularly mogroside V, are retained in the last few columns of the middle columns of the column system.

In one embodiment, the column system is composed of 6 columns that are connected in a consecutive manner. In the first stage, an aqueous alcoholic solution comprising a low purity mogrosides mixture with 34.73% (w/w on dry basis) comprising Mogroside V 19.47%, 11-oxo-Mogroside V 5.60%, Siamenoside I 5.20%, and Grosmomoside I 4.46% was passed through the column system; then each column was eluted with pure alcohol for total elution in order to check the retentions of mogrosides by each column. The results of the total elution from the first stage are summarized in Table 2.

TABLE 2

Mogrosides distribution after first stage

| Mogrosides, | | Columns | | | | | |
|---|---|---|---|---|---|---|---|
| % w/w dry basis | Initial | I | II | III | IV | V | VI |
| Siamenoside I | 5.20 | 2.90 | 11.30 | 8.60 | 4.10 | 2.81 | 1.52 |
| Grosmomoside I | 4.46 | 2.80 | 9.66 | 7.50 | 3.13 | 2.19 | 1.48 |
| 11-oxo-mogroside V | 5.60 | 1.50 | 2.30 | 3.30 | 9.37 | 11.30 | 5.80 |
| Mogroside V | 19.47 | 2.73 | 2.33 | 17.94 | 40.32 | 44.54 | 8.96 |
| TM content | 34.73 | 9.93 | 25.59 | 37.34 | 56.92 | 60.84 | 17.76 |

In another embodiment of present invention, the second stage of the purification process comprises washing the columns with retained mogrosides from the first stage to remove residual impurities which still remain after the first stage of separation in order to increase further the purity level of final products. In one embodiment, the columns are sequentially washed with an acidic aqueous or aqueous alcoholic solution, a basic aqueous or aqueous alcoholic solution, and an aqueous alcoholic solution. The water to alcohol ratio (vol/vol) in aqueous alcoholic solution is 99.9:0.1 to 60:40. The removal of impurities is carried out either from each column separately (parallel connection) or more than one consecutively (serial) connected column groups. Similar to the first stage, each column was eluted with pure alcohol for total elution in order to check the retentions of mogrosides by each column. The results of the total elution from the second stage with the usage of the same low purity mogrosides mixture and the same 6 column system as in the first stage are summarized in Table 2.

TABLE 3

Mogrosides distribution after second stage

| Mogrosides, | | Columns | | | | | |
|---|---|---|---|---|---|---|---|
| % w/w dry basis | Initial | I | II | III | IV | V | VI |
| Siamenoside I | 5.20 | 5.28 | 20.41 | 14.77 | 6.26 | 4.03 | 2.56 |
| Grosmomoside I | 4.46 | 5.09 | 17.45 | 12.88 | 4.73 | 3.16 | 2.54 |
| 11-oxo-mogroside V | 5.60 | 2.73 | 4.15 | 5.67 | 14.34 | 16.25 | 9.85 |
| Mogroside V | 19.47 | 4.96 | 4.21 | 30.81 | 61.52 | 64.05 | 15.22 |
| TM content | 34.73 | 18.06 | 46.23 | 64.13 | 86.85 | 87.49 | 30.16 |

In one embodiment of present invention, the third stage of the purification process comprises eluting the middle section columns (e.g., columns IV and V) with an aqueous alcoholic solution, where water to alcohol ratio (vol/vol) of the aqueous alcoholic solution is 60:40 to 0.1:99.9. The elution is carried out either from each column separately (parallel connection) or more than one consecutively (serial) connected column groups. The elution results in high purity mogrosides.

In one embodiment, the fourth stage of the purification process comprises removing alcohol from mogrosides eluate obtained after the third stage and further concentrating and drying the mogrosides eluate to obtain a dried highly purified mixture of mogrosides. Any method known to art may be used for ethanol removal, concentration and drying.

In one embodiment, the low purity fractions are combined and subjected to repeated purification from the first stage to the fourth stage as described above.

In one embodiment, the high purity fractions are combined and dried to produce high mogroside V content highly purified mixture of mogrosides having TM content of 87.18% (w/w on dry basis) comprising Mogroside V 62.82%, 11-oxo-Mogroside V 15.32%, Siamenoside I 5.11%, and Grosmomoside I 3.92%.

In one embodiment, the purification process of the present invention further comprises filtering with the usage of ultrafiltration and/or nanofiltration membranes. Membranes with molecular weight cut-off (MWCO) size of 1000, 1500 and 2000 are used. Highly purified mogroside mixture comprising Mogroside V 62.82%, 11-oxo-Mogroside V 15.32%, Siamenoside I 5.11%, and Grosmomoside I 3.92% was dissolved in aqueous alcohol solution with alcohol content of 0-100% (vol/vol) preferably 0-50%, to make a solution with total solids content of 0.1-50% (wt/vol), preferably 0.5-10%. The resulted solution was consecutively passed through ultrafiltration and/or nanofiltration membranes with MWCO 1000, 1500, 2000 and 2500. A stirred cell membrane system from Sterlitech Corp. (USA) was used for this purpose. Anyway any suitable filtration system known to art may be used for this purpose. Non-limiting examples of membrane manufacturers are Koch Membrane Systems Inc. (USA), GE-Osmonics (USA), Alfa Laval (Sweden). Flat sheet, hollow fiber, spiral and other membranes may be used. Diafiltration was used to increase membrane filtration process efficiency. Depending on membrane size the retentate or permeate contained the main amount of mogrosides. After each membrane treatment the mogroside containing fraction (retentate or permeate) was concentrated or diluted again till total solids content 0.1-50% (wt/vol) preferably 0.5-10% and passed through the next membrane. The solution was passed through increasing membrane sizes (from MWCO 1000 to 2500). Anyway other order of membrane is also possible. After membrane treatment highly purified mogroside mixture was obtained comprising Mogroside V 67.13%, 11-oxo-Mogroside V 16.31%, Siamenoside I 5.51%, and Grosmomoside I 4.10% (dry basis).

The high purity mogrosides can be used either alone or in combination with other high intensity sweeteners in food, beverage, pharmaceutical composition, tobacco, nutraceutical, oral hygienic composition, or cosmetic. The other high intensity sweeteners include steviol glycosides including a purified sweet steviol glycoside mixture, stevioside, rebaudioside A, rebaudioside B, rebaudioside C, rebaudioside D, rebaudioside E, rebaudioside F, dulcoside A, dulcoside B, rubusoside, and stevia; siamenoside; mogroside IV; mogroside V; Luo Han Guo sweetener; monatin and its salts (monatin SS, RR, RS, SR); glycyrrhizic acid and its salts; curculin; thaumatin; monellin; mabinlin; brazzein; hernandulcin; phyllodulcin; glycyphyllin; phloridzin; trilobatin; baiyunoside; oslandin; polypodoside A; pterocaryoside A;

pterocaryoside B; mukurozioside; phlomisoside I; periandrin I; abrusoside A; cyclocarioside I; and combinations thereof.

The following examples are provided for illustrating the process and column system of the present invention.

Example 1

Purification of High Purity Mogrosides 100 g of luo han guo extract (w/w on dry basis) comprising Mogroside V 19.47%, 11-oxo-Mogroside V 5.60%, Siamenoside I 5.20%, and Grosmomoside I 4.46% (TM content 34.73%) was dissolved in 2.4 liters of deionized water. The solution was passed through 6 consecutively connected 200 mL columns packed with Diaion® HP (Mitsubishi Chemical Corp) macroporous adsorbent. 2.4 L deionized water was subsequently passed through the system. Further the columns were separately washed with 2 volumes of 0.5% HCl, then with water until neutral pH, then with 0.5% NaOH and again with water until neutral pH of washing waters is achieved. Then the columns were separately washed with 10% Ethanol. Then the columns were eluted with 50% Ethanol. Columns 4 and 5 were connected consecutively. The eluate of column 4 and 5 was evaporated under vacuum for ethanol removal. Obtained aqueous solution was spray dried to yield 31 g of highly purified mogroside mixture comprising Mogroside V 62.82%, 11-oxo-Mogroside V 15.32%, Siamenoside I 5.11%, and Grosmomoside I 3.92% (on dry basis).

Example 2

Membrane Purification.

100 g of high purity mogrosides prepared according to EXAMPLE 1 comprising Mogroside V 62.82%, 11-oxo-Mogroside V 15.32%, Siamenoside I 5.11%, and Grosmomoside I 3.92% (on dry basis) was dissolved in 2.4 liters of deionized water. The obtained solution was further passed through stirred cell membrane system (Sterlitech Corp., USA). The solution was passed through GE Osmonics 2500 MWCO membrane. The permeate which contained the mogrosides was concentrated to 5% solids and further passed through 1000MWCO membrane. The retentate which contained the mogrosides was concentrate and dried to yield 90 g powder containing Mogroside V 67.13%, 11-oxo-Mogroside V 16.31%, Siamenoside I 5.51%, and Grosmomoside I 4.10% (dry basis).

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

I claim:

1. A high purity mogrosides mixture comprising:
   Mogroside V in the range of 60-70wt %;
   11-oxo-Mogroside V in the range of 10-20wt %;
   Siamenoside I in the range of 3-7wt %; and
   Grosmomoside I in the range of 2-6wt %.

2. A sweetener mixture comprising the high purity mogrosides mixture of claim 1, wherein the high purity mogrosides mixture is blended with another high intensity sweetener.

3. The sweetener mixture comprising the high purity mogrosides mixture of claim 2, wherein the another high intensity sweetener is selected from the group consisting of steviol glycosides including a purified sweet steviol glycoside mixture, stevioside, rebaudioside A, rebaudioside B, rebaudioside C, rebaudioside D, rebaudioside E, rebaudioside F, dulcoside A, dulcoside B, rubusoside, and stevia; siamenoside; mogroside IV; mogroside V; Luo Han Guo sweetener; monatin and its salts (monatin SS, RR, RS, SR); glycyrrhizic acid and its salts; curculin;
   thaumatin; monellin; mabinlin; brazzein; hernandulcin; phyllodulcin; glycyphyllin; phloridzin;
   trilobatin; baiyunoside; osladin; polypodoside A; pterocaryoside A; pterocaryoside B;
   mukurozioside; phlomisoside I; periandrin I; abrusoside A; cyclocarioside I; and combinations thereof.

4. A product comprising the high purity mogrosides mixture of claim 2.

5. The product of claim 4, wherein the product is selected from the group consisting of food, beverage, pharmaceutical composition, tobacco, nutraceutical, oral hygienic composition, or cosmetic.

* * * * *